(12) United States Patent
Rowan et al.

(10) Patent No.: US 12,319,804 B2
(45) Date of Patent: *Jun. 3, 2025

(54) HIGH INTERNAL PHASE EMULSION FOAM HAVING CELLULOSE NANOPARTICLES

(71) Applicants: The Procter & Gamble Company, Cincinnati, OH (US); Case Western Reserve University, Cleveland, OH (US)

(72) Inventors: Stuart J. Rowan, Cleveland, OH (US); Donald L. Feke, Chesterland, OH (US); Vahid Karimkhani, Cleveland, OH (US); Ica Manas-Zloczower, Orange, OH (US); Boran Zhao, Cleveland, OH (US); Wade Monroe Hubbard, Jr., Wyoming, OH (US); Maxwell Joseph Wingert, Liberty Township, OH (US); Steven Ray Merrigan, West Chester, OH (US)

(73) Assignees: The Procter & Gamble Company, Cincinnati, OH (US); Case Western Reserve University, Cleveland, OH (US)

( * ) Notice: Subject to any disclaimer, the term of this patent is extended or adjusted under 35 U.S.C. 154(b) by 40 days.

This patent is subject to a terminal disclaimer.

(21) Appl. No.: 18/482,108

(22) Filed: Oct. 6, 2023

(65) Prior Publication Data

US 2024/0034850 A1    Feb. 1, 2024

Related U.S. Application Data

(63) Continuation of application No. 15/464,733, filed on Mar. 21, 2017, now Pat. No. 11,814,496.

(60) Provisional application No. 62/311,092, filed on Mar. 21, 2016.

(51) Int. Cl.

| | | |
|---|---|---|
| A61F 13/53 | (2006.01) |
| C08F 2/32 | (2006.01) |
| C08F 2/44 | (2006.01) |
| C08F 220/18 | (2006.01) |
| C08F 222/10 | (2006.01) |
| C08J 9/00 | (2006.01) |
| C08J 9/28 | (2006.01) |

(52) U.S. Cl.
CPC ............. *C08J 9/0061* (2013.01); *C08F 2/32* (2013.01); *C08F 2/44* (2013.01); *C08J 9/0085* (2013.01); *C08J 9/009* (2013.01); *C08J 9/28* (2013.01); *C08J 9/283* (2013.01); *A61F 2013/530817* (2013.01); *C08J 2201/026* (2013.01); *C08J 2201/028* (2013.01); *C08J 2201/0504* (2013.01); *C08J 2207/12* (2013.01); *C08J 2333/06* (2013.01); *C08J 2333/08* (2013.01); *C08J 2401/02* (2013.01)

(58) Field of Classification Search
CPC .......... C08F 2/32; C08F 2/44; C08J 2201/028
See application file for complete search history.

(56) References Cited

U.S. PATENT DOCUMENTS

| | | |
|---|---|---|
| 5,650,222 A | 7/1997 | Desmarais et al. |
| 6,365,642 B1 | 4/2002 | Dyer et al. |
| 11,814,496 B2 | 11/2023 | Rowan et al. |
| 2008/0281003 A1 | 11/2008 | Akay |
| 2010/0261803 A1 | 10/2010 | Bismarck |
| 2011/0117319 A1 | 5/2011 | Yano et al. |
| 2011/0160320 A1 | 6/2011 | Merrigan et al. |
| 2011/0160689 A1 | 6/2011 | Merrigan et al. |
| 2011/0198282 A1 | 8/2011 | Chu et al. |
| 2014/0073706 A1 | 3/2014 | Capron et al. |
| 2015/0010746 A1 | 1/2015 | Oomori |
| 2015/0259500 A1 | 9/2015 | Dyer |
| 2015/0273420 A1 | 10/2015 | Capron et al. |
| 2017/0267827 A1 | 9/2017 | Rowan |

FOREIGN PATENT DOCUMENTS

| | | |
|---|---|---|
| CN | 104177547 A | 3/2014 |
| CN | 103992425 A | 8/2014 |
| WO | 2010058148 A1 | 5/2010 |

OTHER PUBLICATIONS

PCT Search Report and Written Opinion for PCT/US2017/023354 dated Jul. 3, 2017, 15 pages.
All Office Actions; U.S. Appl. No. 15/464,733, filed Mar. 21, 2017.
Capron et al., Surfactant-Free High Internal Phase Emulsions Stabilized by Celluose N anocrystals, Biomacromolecules (2013 ), 14, pp. 291-296.
Carrillo et al., Cellulose Nanofibrils for One-step Stabilization of Multiple Emulsions (W /0/W) Based on Soybean Oils, Journal of Colloid and Interface Science,445 (2015), pp. 166-173.
Isogai et al. , "Tempo-Oxidized Cellulose Nanofibers", The Royal Society of Chemistry, 2011, pp. 71-85.
Lee et al., Phase Behavior of Medium and High Internal Phase Water-in-Oil Emulsions Stabilized Solely by Hydrophobized Bacterial Cellulose Nanofibrils, Langmuir 2014,30, pp. 452-460.

*Primary Examiner* — Melissa A Rioja
(74) *Attorney, Agent, or Firm* — Amanda Herman Berghauer (57) ABSTRACT

A High Internal Phase Emulsion (HIPE) foam having cellulose nanoparticles.

20 Claims, 3 Drawing Sheets

HIGH INTERNAL PHASE EMULSION FOAM HAVING CELLULOSE NANOPARTICLES

FIELD OF THE INVENTION

This application relates to a foam templated from a High Internal Phase Emulsion (HIPE) having cellulose nanoparticles.

BACKGROUND OF THE INVENTION

An emulsion is a dispersion of one liquid in another liquid and generally is in the form of a water-in-oil (or oil in water) mixture having an aqueous or water phase dispersed within a substantially immiscible continuous oil phase (or an oil phase dispersed within a continuous aqueous phase). Water-in-oil emulsions having a high ratio of dispersed aqueous phase to continuous oil phase are known in the art as High Internal Phase Emulsions, also referred to as "HIPE" or HIPEs. At relatively high dispersed aqueous phase to continuous oil phase ratios the continuous oil phase becomes essentially a thin film separating and coating the droplet-like structures of the internal, dispersed aqueous phase. In one embodiment the continuous oil phase of a water-in-oil HIPE comprises one or more polymerizable monomers. These monomers can be polymerized, forming a cellular structure, for example a foam, having a cell size distribution defined by the size distribution of the dispersed, aqueous phase droplets. Polymerization of the monomers starts upon the activation of an initiator and continues during the curing process. The curing process is often at the end or near the end of the foam forming process; after which the HIPE foam is prepared for its future uses.

Current HIPE formulations continue to be difficult to process. As such, it would be beneficial to create a HIPE that has improved physical or structural properties such as a compression modulus, while not sacrificing other desirable properties, such as wettability and stability of the overall foam.

Accordingly, there is a need for HIPE foams having an improved compression modulus and fluid uptake.

SUMMARY OF THE INVENTION

A High Internal Phase Emulsion foam formed by polymerizing a High Internal Phase Emulsion is disclosed. The High Internal Phase Emulsion having a) an oil phase including a monomer; a cross-linking agent; an emulsifier; and cellulose nanoparticles; and b) an aqueous phase.

A High Internal Phase Emulsion foam formed by polymerizing a High Internal Phase Emulsion is disclosed. The High Internal Phase Emulsion having a) an oil phase including a monomer; a cross-linking agent; and an emulsifier; and b) an aqueous phase having a cellulose nanoparticle.

DETAILED DESCRIPTION OF THE INVENTION

The present invention relates to a poly-High Internal Phase Emulsion (HIPE) foam incorporating cellulose nanoparticles. HIPEs of the present invention comprise an oil phase containing monomers and an aqueous phase. The HIPE may be produced in a batch system or using a continuous process, for example by having a HIPE deposited on a belt, such as an endless belt. While on the belt the HIPE are moved to a heating zone, where the monomers are polymerized to form a HIPE foam.

A High Internal Phase Emulsion (HIPE) comprises two phases, one being an oil rich phase (greater than 50% oil) and the other being a water rich phase (greater than 50% water). A HIPE may be an oil in water emulsion or a water in oil emulsion that creates a PolyHIPE foam. As used herein, a PolyHIPE foam refers to a high internal phase emulsion prepared in which the continuous phase contains one or more monomeric species, and polymerization is initiated producing a novel type of highly porous material as described in High Internal Phase Emulsion (HIPEs)—Structure Properties, and Use in Polymer Preparation found in Advances of Polymer Science Vol. 126, 1996 page 190.

The oil phase comprising monomers that are polymerized to form a HIPE foam and an emulsifier to help stabilize the HIPE. The aqueous phase of a HIPE comprises water, and may also comprise one or more components, such as initiator, photoinitiator, or electrolyte, wherein in certain embodiments, the one or more components are at least partially water soluble. Either the oil phase or the aqueous phase may comprise cellulose nanoparticles.

Applicants have found that the use of cellulose nanoparticles may impact the wet HIPE foam compressive modulus. Specifically, the use of cellulose nanoparticles may lead to an increase of between 1.1 to 25 times the compressive modulus. In other words the compressive modulus for a wet HIPE foam is a fraction of the compressive modulus for a wet HIPE foam with cellulose nanoparticles. For example, the HIPE foam having cellulose nanoparticles may have a compressive modulus that is a multiple, such as, between 2 times and 24 times the compressive modulus of a HIPE foam without cellulose nanoparticles, such as, for example, 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 3 times, 3.5 times, 4 times, 4.5 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, or 25 times versus a HIPE not having cellulose nanoparticles. HIPE foams having cellulose nanoparticles may exhibit a compressive modulus that is between 10 KPa and 400 KPa, such as, for example, between 20 KPa and 350 KPa, between 20 KPa and 300 Kpa, between 35 KPa and 250 KPa, such as, 30, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, 260, 27, 280, 290, 300, 310, 320, 330, 340, 350, 360, 370, 380, or 390 KPa.

Further, when added to the HIPE, the cellulose nanoparticles led to an increase in the wettability of the HIPE foam. Wettability may be measured by fluid uptake which may be categorized using a Washburn coefficient. The use of cellulose nanoparticles may lead to an increase in the Washburn coefficient of greater than $1*10^4$ mg$^2$/s, such as, between $1*10^4$ mg$^2$/s and $1*10^6$ mg$^2$/s, such as $2.35*10^5$ mg$^2$/s and $3.1*10^4$ mg$^2$/s for a sample that is a 15 mm thick disc with a 25 mm diameter.

The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 0.1% to about 20% by weight of the oil phase. The emulsion may be formed at an emulsification temperature of from about 10° C. to about 130° C. and in certain embodiments from about 50° C. to about 100° C.

In general, the monomers will comprise from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also comprise from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate: acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. In certain cases, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type comprise styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995, and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they comprise between about 0.1% and about 20%, in certain embodiments from about 2% to about 15%, and in certain other embodiments from about 3% to about 12% by weight of the oil phase. In certain embodiments, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a coemulsifier.

Photoinitiators may comprise between about 0.05% and about 10%, and in certain embodiments between about 0.2% and about 10% by weight of the oil phase. Lower amounts of photoinitiator allow light to better penetrate the HIPE, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The oil phase may further contain one or more cellulose nanoparticles. Cellulose nanoparticles may be selected from Microfibrillated cellulose (MFC), Microcrystalline cellulose (MCC), Nanocrystalline cellulose (NCC), Nano cellulose or Nanocellulose or Bacterial nanocellulose, Nanofibrillated cellulose (NFC), Cellulose nanofiber(s), Cellulose microfibril or cellulosic microfibril(s), Cellulose nanorod or cellulosic nanorod(s), Cellulose nanocrystal(s) (CNC), or combinations thereof. The cellulose nanoparticles may have a diameter between, for example, 1 to 20 nm wherein the diameter is the smallest dimension on the particles. The cellulose nanoparticles may have a diameter greater than 20 nm. Cellulose nanoparticles have at least one dimension in the nano scale.

Cellulose nanofibers may include Cellulose nanofibril(s), cellulosic nanofiber(s), Nanocellulose fiber(s), cellulosic nanofibril(s), micro-cellulosic fiber(s), and micro-cellulose fiber(s).

Cellulose nanocrystals may include Cellulosic nanocrystal(s), nanocrystalline cellulose, cellulose nanowhisker(s), cellulosic nanowhisker(s), Cellulose whisker(s), and cellulosic whisker(s).

Cellulose nanoparticles may be biosourced. Cellulose nanoparticles may be sourced from tunicates, Miscanthus x. Giganteus, microcrystalline cellulose, wood, cotton, algae, bacteria, and most plants.

The cellulose nanoparticles may be modified to make the nanoparticles more hydrophobic prior to being incorporated into the oil phase or the aqueous phase. Modifiers include, without limitation, 2,2,6,6-tetramethylpyperidine-1-oxyl (TEMPO) with sodium hypochlorite (NaClO) (TEMPO/NaClO) oxidized, butyric anhydride (BA), isopropyldimethylchlorosilane (IPDMSiCl), 2,2,6,6-tetramethylpyperidine-1-oxyl (TEMPO) with sodium hypochlorite (NaClO) (TEMPO/NaClO) oxidized and then cetyltrimethylammonium bromide (CTAB), TEMPO oxidized and then Octadecylamine (CONH-C18), (2-dodecen-1-yl)succinic anhydride (DDy SA), Sulfuric acid ($SO_3^-$) and then (2-dodecen-1-yl)succinic anhydride (DDy SA), 2,2,6,6-tetramethylpyperidine-1-oxyl with sodium hypochlorite (TEMPO/NaClO) oxidized and then (2-dodecen-1-yl)succinic anhydride (DDy SA), Octadecyl isocyanate (U-C18), Hexyl isocyanate (U-C6), 2-ethylhexyl isocyanate, Acetic anhydride (A), and combinations thereof. Modifiers may further include succinic anhydride and isocyanates.

Applicants have found that the addition of cellulose nanoparticles that have been modified by one or more of the listed chemical modifiers creates a HIPE foam with a compression modulus that is a multiple of the compression modulus of a HIPE without the chemically modified cellulose nanoparticles. Further, as shown in the table below, simply adding unfunctionalized or carboxylic acid functionalized cellulose nanoparticles may not lead to the improved compression modulus. It has been found that by adding the functionalized cellulose nanoparticles, one can effectively create a HIPE foam that has an improved compression modulus.

Cellulose nanoparticles may be used at less than 10 percent of the oil phase, such as, for example between 0.001% and 5% of the oil phase, such as, for example 0.05% of the oil phase, 0.1% of the oil phase, 0.15% of the oil phase, 0.2% of the oil phase, 0.25% of the oil phase, 0.3% of the oil phase, 0.35% of the oil phase, 0.4% of the oil phase, 0.45% of the oil phase, 0.5% of the oil phase, 0.55% of the oil phase, 0.6% of the oil phase, 0.65% of the oil phase, 0.7% of the oil phase, 0.75% of the oil phase,0.8% of the oil phase, 0.85% of the oil phase, 0.9% of the oil phase, 0.95% of the oil phase, 1.0% of the oil phase, 1.05% of the oil phase, 1.1% of the oil phase, 1.2% of the oil phase, 1.3% of the oil phase, 1.4% of the oil phase, 1.5% of the oil phase, 1.6% of the oil phase, 1.7% of the oil phase, 1.8% of the oil phase, 1.9% of the oil phase, 2% of the oil phase, 2.1% of the oil phase, 2.2% of the oil phase, 2.3% of the oil phase, 2.4% of the oil phase, 2.5% of the oil phase, 2.6% of the oil phase, 2.7% of the oil phase, 2.8% of the oil phase, 2.9% of the oil phase, 3.0% of the oil phase, 3.1% of the oil phase, 3.2% of the oil phase, 3.3% of the oil phase, 3.4% of the oil phase, 3.5% of the oil phase, 3.6% of the oil phase, 3.7%o of the oil phase, 3.8% of the oil phase, 3.9% of the oil phase, 4.0% of the oil phase, 4.1% of the oil phase, 4.2% of the oil phase, 4.3% of the oil phase, 4.4% of the oil phase, 4.5% of the oil phase, 4.6% of the oil phase, 4.7% of the oil phase, 4.8% of the oil phase, 4.9% of the oil phase, and 5% of the oil phase.

The dispersed aqueous phase of a HIPE comprises water, and may also comprise one or more components, such as initiator, photoinitiator, or electrolyte, wherein in certain embodiments, the one or more components are at least partially water soluble.

The aqueous phase may further contain one or more cellulose nanoparticles. Cellulose nanoparticles may be selected from Microfibrillated cellulose (MFC), Microcrystalline cellulose (MCC), Nanocrystalline cellulose (NCC), Nano cellulose or Nanocellulose or Bacterial nanocellulose, Nanofibrillated cellulose (NFC), Cellulose nanofiber(s), Cellulose microfibril or cellulosic microfibril(s), Cellulose nanorod or cellulosic nanorod(s), Cellulose nanocrystal(s) (CNC), or combinations thereof.

Cellulose nanofibers may include Cellulose nanofibril(s), cellulosic nanofiber(s), Nanocellulose fiber(s), cellulosic nanofibril(s), micro-cellulosic fiber(s), and micro-cellulose fiber(s).

Cellulose nanocrystals may include Cellulosic nanocrystal(s), cellulose nanowhisker(s), cellulosic nanowhisker(s), Cellulose whisker(s), and cellulosic whisker(s).

Cellulose nanoparticles may be used at less than 2 percent of the aqueous phase, such as, for example between 0.001% and 5% of the aqueous phase, such as, for example 0.05% of the aqueous phase, 0.1% of the aqueous phase, 0.15% of the aqueous phase, 0.2% of the aqueous phase, 0.25% of the aqueous phase, 0.3% of the aqueous phase, 0.35% of the aqueous phase, 0.4% of the aqueous phase, 0.45% of the aqueous phase, 0.5% of the aqueous phase, 0.55% of the aqueous phase, 0.6% of the aqueous phase, 0.65% of the aqueous phase, 0.7% of the aqueous phase, 0.75% of the aqueous phase,0.8% of the aqueous phase, 0.85% of the aqueous phase, 0.9% of the aqueous phase, 0.95% of the aqueous phase, 1.0% of the aqueous phase, 1.05% of the aqueous phase, 1.1% of the aqueous phase, 1.2% of the aqueous phase, 1.3% of the aqueous phase, 1.4% of the aqueous phase, 1.5% of the aqueous phase, 1.6% of the aqueous phase, 1.7% of the aqueous phase, 1.8% of the aqueous phase, 1.9% of the aqueous phase, 2% of the aqueous phase, 2.1% of the aqueous phase, 2.2% of the aqueous phase, 2.3% of the aqueous phase, 2.4% of the aqueous phase, 2.5% of the aqueous phase, 2.6% of the aqueous phase, 2.7% of the aqueous phase, 2.8% of the aqueous phase, 2.9% of the aqueous phase, 3.0% of the aqueous phase, 3.1% of the aqueous phase, 3.2% of the aqueous phase, 3.3% of the aqueous phase, 3.4% of the aqueous phase, 3.5% of the aqueous phase, 3.6% of the aqueous phase, 3.7%o of the aqueous phase, 3.8% of the aqueous phase, 3.9% of the aqueous phase, 4.0% of the aqueous phase, 4.1% of the aqueous phase, 4.2% of the aqueous phase, 4.3% of the aqueous phase, 4.4% of the aqueous phase, 4.5% of the aqueous phase, 4.6% of the aqueous phase, 4.7% of the aqueous phase, 4.8% of the aqueous phase, 4.9% of the aqueous phase, and 5% of the aqueous phase.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include hydrogen peroxide, lauryl peroxide, t-butyl hydrogen peroxide, other suitable peroxides, ammonium persulfate, sodium persulfate, potassium persulfate, 2,2'-azobis(N,N'-dimethyleneisobutyramidine) dihydrochloride, and other suitable azo initiators, redox couples such as persulfate-bisulfate, persulfate- ascorbic acid and others. In certain embodiments, to reduce the potential for premature polymerization which may clog the emulsification system, addition of the initiator may be added just after or near the end of emulsification. In certain embodiments a small amount of inhibitor may be added to inhibit polymerization during emulsification.

Photoinitiators present in the aqueous phase may be at least partially water soluble and may comprise between about 0.05% and about 10%, and in certain embodiments between about 0.2% and about 10% by weight of the oil phase. Lower amounts of photoinitiator allow light to better penetrate the HIPE which can provide for polymerization deeper into the HIPE. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone,4-dimethylamino-4'-carboxymethoxydibenzalacetone; and 4,4'-disulphoxymethoxydibenzalacetone. Other suitable photoinitiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain embodiments, HIPE foams may have one or more layers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct layers that differ with regard to their chemical composition, physical properties, or both; for example layers may differ with regard to one or more of foam density, polymer composition, specific surface area, or pore size (also referred to as cell size). For example, for a HIPE foam if the difference relates to pore size, the average pore size in each layer may differ by at least about 20%, in certain embodiments by at least about 35%, and in still other embodiments by at least about 50%. In another example, if the differences in the layers of a HIPE foam relate to density, the densities of the layers may differ by at least about 20%, in certain embodiments by at least about 35%, and in still other embodiments by at least about 50%. For instance, if one layer of a HIPE foam has a density of 0.020 g/cc, another layer may have a density of at least about 0.024 g/cc or less than about 0.016 g/cc, in certain embodiments at least about 0.027 g/cc or less than about 0.013 g/cc, and in still other embodiments at least about 0.030 g/cc or less than about 0.010 g/cc. If the differences between the layers are related to the chemical composition of the HIPE or HIPE foam, the differences may reflect a relative amount difference in at least one monomer component, for example by at least about 20%, in certain embodiments by at least about 35%, and in still further embodiments by at least about 50%. For instance, if one layer of a HIPE or HIPE foam is composed of about 10% styrene in its formulation, another layer of the HIPE or HIPE foam should be composed of at least about 12%, and in certain embodiments of at least about 15%.

A HIPE foam having separate layers formed from differing HIPEs, as explained in more detail below, provides a HIPE foam with a range of desired performance characteristics. For example, a HIPE foam comprising a first and second foam layer, wherein the first foam layer has a relatively larger pore or cell size, than the second layer, when used in an absorbent article may more quickly absorb incoming fluids than the second layer. By way of example when used in an absorbent articled the first foam layer may be layered over the second foam layer having relatively smaller pore sizes, as compared to the first foam layer, which exert more capillary pressure and drain the acquired fluid from the first foam layer, restoring the first foam layer's ability to acquire more fluid. HIPE foam pore sizes may range from 1 to 200 µm and in certain embodiments may be less than 100 µm. HIPE foams of the present invention having two major parallel surfaces may be from 0.05 to 10 mm thick, and in certain embodiments 2 mm to 8 mm. The desired thickness of a HIPE will depend on the materials used to form the HIPE, the speed at which a HIPE is deposited on a belt, and the intended use of the resulting HIPE foam.

The HIPE foams of the present invention are relatively open-celled. This refers to the individual cells or pores of the HIPE foam being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present invention, a HIPE foam is considered "open-celled" if at least about 80% of the cells in the HIPE foam that are at least 1 µm in size are in fluid communication with at least one adjoining cell.

In addition to being open-celled, in certain embodiments HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures (as described hereafter), or combinations of both.

In certain embodiments, for example when used in certain absorbent articles, a HIPE foam may be flexible and exhibit an appropriate glass transition temperature (Tg). The Tg represents the midpoint of the transition between the glassy and rubbery states of the polymer. In general, HIPE foams that have a higher Tg than the temperature of use can be very strong but will also be very rigid and potentially prone to fracture. In certain embodiments, regions of the HIPE foams of the current invention which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain embodiments, the Tg of this region will be less than about 30° C. for foams used at about ambient temperature conditions, in certain other embodiments less than about 20° C. For HIPE foams used in applications wherein the use temperature is higher or lower than ambient, the Tg of the continuous region may be no more that 10° C. greater than the use temperature, in certain embodiments the same as use temperature, and in further embodiments about 10° C. less than use temperature wherein flexibility is desired. Accordingly, monomers are selected as much as possible that provide corresponding polymers having lower Tg's.

The HIPE foams of the present invention may be used as absorbent core materials in absorbent articles, such as feminine hygiene articles, for example pads, pantiliners, and tampons; disposable diapers; incontinence articles, for example pads, adult diapers; homecare articles, for example wipes, pads, towels; and beauty care articles, for example pads, wipes, and skin care articles, such as used for pore cleaning.

To produce a HIPE using the above, an aqueous phase and an oil phase are combined in a ratio between about 8:1 and 140:1. In certain embodiments, the aqueous phase to oil phase ratio is between about 10:1 and about 75:1, and in certain other embodiments the aqueous phase to oil phase ratio is between about 13:1 and about 65:1. This is termed the "water-to-oil" or W:O ratio can be used to determine the density of the resulting HIPE foam. As discussed, the oil phase may contain one or more of monomers, comonomers, photoinitiators, crosslinkers, and emulsifiers, as well as optional components. The water phase will contain water and in certain embodiments one or more components such as electrolyte, initiator, or optional components.

The HIPE can be formed from the combined aqueous and oil phases by subjecting these combined phases to shear agitation in a mixing chamber or mixing zone. The combined aqueous and oil phases are subjected to shear agitation produce a stable HIPE having aqueous droplets of the desired size. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992, and U.S. Pat. No. 5,827,909 (DesMarais) issued on Oct. 27, 1998.

In certain embodiments for a continuous process the HIPE can be withdrawn or pumped from the mixing zone and transported to a heating zone, such as a curing oven by being deposited on to a belt travelling in a substantially horizontal direction. An initiator may be present in the aqueous phase, or an initiator may be introduced during the HIPE making process, and in certain embodiments, after the HIPE has been formed but before the HIPE has been deposited on to the belt. The HIPE may be deposited on to the belt through one or more depositing devices such as a die, sprayer, or caster. Two or more distinct HIPEs can be produced, which after polymerization will form two or more distinct layers in a HIPE foam, for example a first HIPE and a second HIPE, wherein each HIPE may have an individual composition (aqueous and oil phases) or individual combinations of properties, for example pore dimensions, mechanical properties, and the like, that differs from the other HIPEs. The individual HIPEs can be formed from one or more individual oil phases and one or more individual aqueous phases, and combinations thereof. For example, individual HIPEs can be formed from a single oil phase combined with 2 or more different aqueous phases, or a single aqueous phase combined with 2 or more individual oil phases.

The individual aqueous and oil phases enter separate mixing zones and then are deposited the same way as individual HIPEs. For example, in a continuous process of the present invention a first die can deposit one HIPE layer on to a belt then the same die or a second die could deposit a second HIPE on top of the first HIPE. In certain embodiments, the top second HIPE may have a lower concentration of photoinitiator as compared to the bottom first HIPE such that a similar amount of radicals is formed in both HIPE layers. In another embodiment using the previously described continuous method a die could deposit HIPEs adjacently on to a belt where the individual HIPEs may or may not overlap each other, or any other means of moving one or more HIPEs from a mixing zone to produce a HIPE foam.

Examples of belts may include endless belts made of one or more metals, a resin, or combinations thereof; or sheet materials such as films that may be positioned on the belt and moving therewith. The average thickness of the HIPE, as measured from the surface of the HIPE that is in contact with the belt to the opposing HIPE surface, can be adjusted by the movement speed of the belt, the flow of HIPE deposited on the belt, or the configuration of one or more depositing devices used to deposit the HIPE on a belt.

The belt can be any thickness or shape suitable for producing a HIPE foam. Further, the surface of the belt upon which the HIPE will be deposited, can be substantially smooth or may comprise depressions, protuberances, or combinations thereof. The protuberances or depressions may be arranged in any formation or order and can be used to provide patterns, designs, markings or the like to HIPE foam. The belt may comprise one or more materials suitable for the polymerization conditions (various properties such as heat resistance, weatherability, surface energy, abrasion resistance, recycling property, tensile strength and other mechanical strengths) and may comprise at least one material from the group including films, non-woven materials, woven materials, and combinations thereof. Examples of films include, fluorine resins such as polytetrafluoroethylene, tetrafluoroethylene-perfluoroalkylvinyl ether copolymers, tetrafluoroethylene-hexafluoropropylene copolymers, and tetrafluoroethylene-ethylene copolymers; silicone resins such as dimethyl polysiloxane and dimethylsiloxane-diphenyl siloxane copolymers; heat-resistant resins such as polyimides, polyphenylene sulfides, polysulfones, polyether sulfones, polyether imides, polyether ether ketones, and para type aramid resins; thermoplastic polyester resins such as polyethylene terephthalates, polybutylene terephthalates, polyethylene naphthalates, polybutylene naphthalates, and polycyclohexane terephthalates, thermoplastic polyester type elastomer resins such as block copolymers (polyether type) formed of PBT and polytetramethylene oxide glycol and block copolymers (polyester type) formed of PBT and polycaprolactone may be used. These materials may be used either singly or in mixed form of two or more materials. Further, the belt may be a laminate comprising two or more different materials or two or more materials of the same composition, but which differ in one or more physical characteristics, such as quality or thickness. In certain embodiments the belt or a film positioned on the belt and moving therewith may be transparent to UV light; allowing the UV light from a UV light source positioned below the belt, film or both to polymerize the monomers in a HIPE foam.

In certain embodiments, the belt moves the HIPE into a heating zone where the monomers present in the HIPE are polymerized. Without being bound by theory, it is believed that HIPE foam formation comprises two overlapping processes. These are the polymerization of the monomers and the formation of crosslinks between active sites on adjacent polymer backbones. As used herein the term "polymerize" as in to polymerize monomers to form a HIPE foam, encompass both polymerization of monomers and formation of crosslinks between active sites on adjacent polymer backbones. Crosslinking provides HIPE foams with strength and integrity that is helpful to their further handling and use. The current invention involves increasing the overall level of polymerization and cross-linking, thereby reducing the amount of unpolymerized monomer in the HIPE foam. Polymerization can be initiated prior to reaching the heating zone by, for example, preparing the HIPE at a temperature sufficient to begin polymerization. However, the HIPE is polymerized beyond the point of shapability or moldability in the heating zone. Heat for the heating zone can be, for example, derived from an oven located above and below the HIPE or surrounding the HIPE. Heat can be from forced air ovens, IR heat lamps, microwave, steam or other suitable source. As an example of using steam the heat zone may be a steam tunnel wherein the HIPE is exposed to steam, thereby achieving highly efficient thermal transfer as water condenses onto the HIPE.

In certain embodiments, the temperature may be elevated in a step-wise manner so as to increase the rate of polymerization, initiate drying, or both as the HIPE becomes more completely polymerized. In addition, the curing of the HIPE may be accomplished by passing the web through a hot liquid bath composed of any hot liquid of sufficient temperature to initiate the curing of the monomers. Polymerization temperatures will vary depending on the type of emulsion being cured, the initiator being used, heat source used, and whether or not the heating zone is sealed, but will typically be above 25° C., often above 50° C. In certain embodiments, polymerization temperatures within the heating zone may reach between about 50° C. and 150° C. The HIPE is maintained in the heating zone for a time sufficient to polymerize at least 75%, preferably at least 90% of the monomers in the oil phase of the HIPE. Sufficient polymerization of the HIPE may be controlled by a combination of the initiator used, the temperature of the heat zone, the efficiency of the heat transfer in the heat zone, the rate at which the HIPE goes through the heat zone and the length of the heat zone.

Following the heat zone the belt moves the mostly polymerized HIPE foam to an Ultraviolet (UV) light zone containing one or more sources of UV light. Exposure of the HIPE foam containing unpolymerized monomers, and in certain embodiments, one or more photoinitiators to the UV light zone initiates polymerization of unpolymerized monomers in the oil phase of the HIPE foam following heat assisted polymerization. An examples of a source of UV light is a UV lamp. There may be one or more sources of UV light used to polymerize the HIPE monomers. A UV light source may be positioned above or below the belt. The sources may be the same or differ. For example, the sources may differ in the wavelength of the UV light they produce or in the amount of time a HIPE is exposed to the UV light source. The light wavelength in the range from about 200 to about 800 nm, and in certain embodiments from about 250 nm to 450 nm, overlaps to at least some degree with the UV light absorption band of the photoinitiator and is of sufficient intensity and exposure duration to substantially complete the polymerization of the unpolymerized monomers. Without being limited to theory it is believed that due to the tendency of emulsions, such as HIPEs, to scatter light, in certain embodiments, long wavelengths in this range should be used because they are better able to penetrate the emulsions. Following the application of UV light the HIPE foam contains less than 400 ppm, in certain embodiments less than 100 ppm, and in certain other embodiments less than detection limits ppm residual or unpolymerized monomer, in less than about 10 minutes, less than about 30 seconds, less than about 10 seconds, or less than about 1 second. In certain embodiments, the entire emulsion making, polymerization, and monomer reduction processes will take less than 20 min, in certain other embodiments in further embodiments less than 15 minutes, and in still further embodiments less than 5 minutes.

Following polymerization, the resulting HIPE foam is saturated with aqueous phase that needs to be removed to obtain substantially dry HIPE foam. In certain embodiments, HIPE foams can be squeezed free of most of the aqueous phase by using compression, for example by running the HIPE foam through one or more pairs of nip rollers. The nip rollers can be positioned such that they squeeze the aqueous phase out of the HIPE foam. The nip rollers can be porous and have a vacuum applied from the inside such that they assist in drawing aqueous phase out of the HIPE foam. In certain embodiments, nip rollers can be positioned in pairs, such that a first nip roller is located above a liquid permeable belt, such as a belt having pores or composed of a mesh-like material, and a second opposing nip roller facing the first nip roller and located below the liquid permeable belt. One of the pair, for example the first nip roller can be pressurized while the other, for example the second nip roller, can be evacuated, so as to both blow and draw the aqueous phase out of the of the HIPE foam. The nip rollers may also be heated to assist in removing the aqueous phase. In certain embodiments, nip rollers are only applied to non-rigid HIPE foams, that is HIPE foams whose walls would not be destroyed by compressing the HIPE foam. In yet a further embodiment, the surface of the nip rollers may contain irregularities in the form of protuberances, depressions, or both such that a HIPE foam can be embossed as it is moving through the nip rollers. When the HIPE has the desired dryness it may be cut or sliced into a form suitable for the intended application.

In certain embodiments, in place of or in combination with nip rollers, the aqueous phase may be removed by sending the HIPE foam through a drying zone where it is heated, exposed to a vacuum, or a combination of heat and vacuum exposure. Heat can be applied, for example, by running the foam though a forced air oven, IR oven, microwave oven or radiowave oven. The extent to which a HIPE foam is dried depends on the application. In certain embodiments, greater than 50% of the aqueous phase is removed. In certain other embodiments greater than 90%, and in still other embodiments greater than 95% of the aqueous phase is removed during the drying process.

As previously discussed, it has been found that the use of cellulose nanoparticles may impact the, wet HIPE foam compressive modulus. Specifically, the use of cellulose nanoparticles may lead to an increase of between 1.1 to 25 times the compressive modulus of the wet HIPE foam without cellulose nanoparticles. As shown in the tables below, HIPE foams having cellulose nanoparticles may exhibit a compressive modulus that is between 20 KPa and 400 KPa.

Without being bound by theory, it is believed that the aspect ratios of the cellulose nanoparticles chosen may also have an impact in the compressive modulus. The mechanical properties of open-cell poly(HIPE)s at the same relative density are mainly dependent on the structure of the foam and the properties of the solid struts. As shown in the tables, the presence of small amounts of cellulose nanoparticles (even below 1 weight percent) with a surface modification appropriate for the oil phase can lead to significant changes in the morphology. In Table 1B, this effect is more than a 10-times increase in certain mechanical properties of the foam such as its modulus. The degree of enhancement in the mechanical properties from a morphology enhancement mechanism will be dependent on the oil phase composition.

Moreover, it has been shown that adding of solid filler particles and reinforcing the poly(HIPE) struts also can lead to enhanced mechanical properties of fabricated foams. Some researchers reported improvement in the mechanical properties of poly(HIPE)s, without changing the morphology, is due to reinforcement provided by the fillers.

Aspect ratios of the CNCs used were between 10 and 130, such as, for example, 20, 30, 40, 50, 60, 70, 80, 90, 100, 110, and 120. As used herein the aspect ratio is a ratio of the length to the width. Fillers with aspect ratio in this range that are added to a polymer can provide reinforcement (as shown in Table 1C) to the composite when the components are compatible. As shown in Table 1A and 1B, adding CNCs improves the structure leading to an increased benefit.

Based on the aspect ratios and the concentration in the oil phase, the composition is expected to be around the percolation threshold of the fillers in the oil phase. As can be seen in table 1C, introducing 1 weight percent BA-Miscanthus x. Giganteus CNC (BA-MxG-CNC) increases the polyHIPE foam modulus. Introducing a high volume fraction of water droplets into the oil phase will cause some orientation of the fillers around the droplets, and droplet to droplet compression will push CNCs together and decrease their distances. This phenomenon may lead to reduction in percolation threshold of the nanoparticles. Therefore, when the third embodiment showed no significant change in morphology unlike the other comparisons, an enhancement in modulus of 54% was observed in the presence of 1 weight percent BA-MxG-CNC (Table 1C). It is believed that this enhancement is based on a reinforcement mechanism.

EXAMPLES

Preparation of High Internal Phase Emulsions (HIPE) and their subsequent polymerization into absorbent foams is described below. The HIPE samples contained cellulose nanoparticles added to either the aqueous phase or the oil phase. Alternatively, the cellulose nanoparticles may be added after the emulsion has been made with additional water (e.g. added through the introduction of an aqueous suspension of the nanoparticles to a previously formulated emulsion).

The HIPE may be created by adding the cellulose nanoparticles using a two-step batch process. The two-step batch process may include making a HIPE and then blending suspension of CNC in an aqueous phase prior to polymerizing the HIPE into a polyHIPE foam.

Alternatively, one may inject cellulose nanoparticles in an aqueous phase into the emulsion as it passes through a pipe. This may be done by injecting cellulose nanoparticles after a HIPE has been made by injecting the cellulose nanoparticles within an aqueous phase into the emulsion phase. The HIPE may then be later polymerized into a polyHIPE foam. Alternatively, one may create a suspension of cellulose nanoparticles in oil and add the suspension to the oil phase in a traditional batch HIPE making process. Alternatively, one may use a two-step batch process including making a HIPE and then blending suspension of CNC in oil prior to polymerizing the HIPE into a polyHIPE foam.

Preparation of Oil Phases

In a first embodiment, five oil phases were created. The first was one without CNCs containing approximately 60-70% 2-ethylhexyl acrylate (2-EHA), 20-30% ethylene glycol dimethacrylate (EGDMA), and 10-20% Polyglycerol succinate (PGS). The PGS surfactant was thoroughly dissolved in the monomer blend.

The second oil phase was created by suspending 0.88 wt% of the unmodified tunicate-based CNCs in the oil phase. This was accomplished by adding the particles slowly and then using a magnetic stir bar overnight. On the following day, ultrasonication of 5 seconds on followed by 5 seconds off repeatedly for a total duration of 1 hour was used. An ice bath was used to minimize temperature gain in the oil phase during ultrasonication.

The remaining oil phases were created by suspending 1 weight % (relative to the monomers) of silylated tunicate CNCs (t-CNC)s in the oil phase and dispersed in it by overnight mixing. The silylated t-CNCs were created following a similar procedure to Goussé et al. The amount of isopropyldimethylchlorosilane (IPDMSiCl) surface modification in the modification reaction varied to the following levels: 2, 4, and 6 times the concentration of the repeat anhydroglucopyranose unit (AGU), which this includes both accessible and non-accessible AGU units. The oil phases, CNC sources, and levels of surface modification are summarized in Table 1A.

In a second embodiment, the oil phase contains approximately 30-40% 2-ethylhexyl methacrylate (2-EMHA) 30-40% (2-EHA), 10-20% EGDMA, and 5-10% PGS. 14 samples were created with this oil phase. The first one was without CNC. The remaining oil phases created by suspending different amount of unmodified CNC, Acetic anhydride-modified CNC, butyric anhydride-modified CNC, or hexylisocyanate-modified CNC via ultrasonication as described above. The oil phases, CNC sources, and levels of surface modification are summarized in Table 1B.

In a third embodiment, the oil phase contains 30-40% 2-EMHA, 30-40% 2-EHA, 10-20% EGDMA, 5-10% PGS, and 0-1% ditallow dimethyl ammonium sulfate (DTD-MAMS). Six samples were created with this oil phase. The first one was without CNC. The remaining oil phases created by suspending different amount of butyric anhydride-modified CNC or hexylisocyanate-modified CNC via ultrasonication as described above. The oil phases, CNC sources, and levels of surface modification are summarized in Table 1C.

Preparation of High Internal Phase Emulsions

High internal phase emulsions were attempted with each oil phase. Sodium persulfate (NaPS) 98% as free radical initiator and sodium chloride (NaCl) as electrolyte were purchased from Sigma Aldrich. The final aqueous phase in the HIPE contained 2 wt. % of NaCl and approximately between 0-1 wt. % of NaPS, relative to the aqueous phase.

142 g of the aqueous solution (2 wt. % solution of NaCl) was heated to 40° C. and added between 0 and 10 mL/min to 8 g of the oil phase, which was kept approximately at the same temperature. Each system was stirred at 300 rpm during addition of the aqueous phase. As shown in Table 1, all cases except for the unmodified t-CNC formed a high internal phase emulsion. The unmodified t-CNC (sample 1B) resulted in a low viscosity material possessing both oil-in-water and water-in-oil emulsions: a broken HIPE.

After completion of adding the 142 g of aqueous phase, the system was mixed for 15 additional minutes and then the initiator solution was added dropwise over 1.5 minute. The resulting reaction mixture is a high internal phase emulsion which was stirred for an additional 5 minutes after which transferred to a series of 10 ml beakers. The beakers were covered with Parafilm and aluminum foil, and put in the oven at ~90 C for 24 hours. The final water to oil ratio was 19:1.

The samples for the second and third embodiment were made similar to that previously described except for the following changes. A total of 144.3 g of aqueous phase was added to 5.71 g of oil phase at a rate of 40 ml/min. The aqueous phase was heated to ~40 ° C. before adding to the oil phase container kept in a heated jacket at 60° C. After completing the addition of the aqueous phase, the emulsion was mixed for more 2 minutes before adding initiator. The resulting mixture is a high internal phase emulsion which was stirred for an additional 5 minutes after which it was transferred to a series of 50 mL centrifuge tubes which were then capped. The final water to oil ratio in all HIPEs was 27:1.

Mechanical Testing of Polymer Foams

Figure 1:
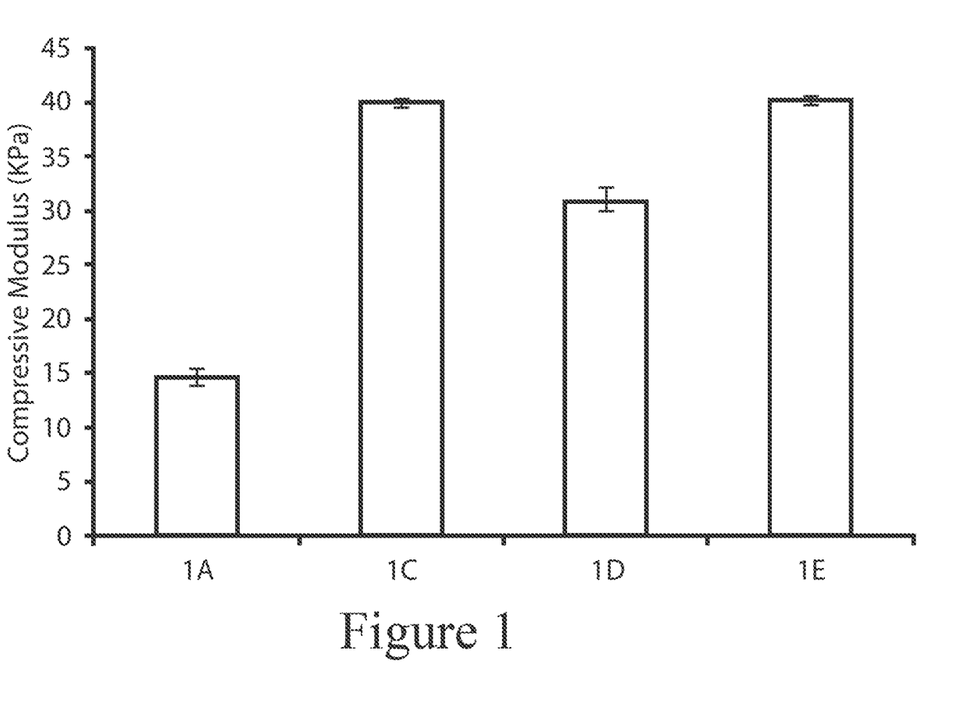
FIG. 1 is a table showing compression modulus.

In order to investigate the influence of silylated t-CNC on the mechanical behavior of the final poly(HIPE) nanocomposites, compression mode stress—strain analysis was done on the wet samples (i.e. not dried). Before doing mechanical tests, samples were soaked in the 2 wt. % NaCl solution (in D.I. water) for at least 1 hour to ensure they were saturated with aqueous phase. Then, the upper 0.5 cm of the sample was cut and removed by a razor blade, in order to remove any rough surface. Samples were cut to disks with 1 cm height. They were again soaked for 5 minutes in the 2 wt.% NaCl solution to ensure they did not lose any aqueous phase. Finally the disks were mounted into the testing machine. Compression testing was carried out using an MTS® universal tensile tester (Model 2525-806, MTS System Corporation, Minnesota, USA). The test occurred at 21° C. ambient temperature. The crosshead speed was kept constant at 1 mm/min. Compressive moduli extracted from the slopes of the linear portions of the stress-strain curves and the values reported are averages of at least three samples in FIG. 1 (Table 1A). FIG. 1 shows the average and standard deviation of the sample 1A, 1C, 1D, and 1E. FIG. 1 demonstrates a 2.0 to 2.5 times improvement in the compressive modulus versus the control, sample 1A, which possesses no CNC particles. Additionally, as shown in Table 1B, the compressive modulus of the samples containing CNC particles was up to seventeen times versus the control sample. In Table 1C, the compressive modulus of the samples containing CNC particles exhibited an increase of up to 54% versus the control.

TABLE 1A

| Sample name | CNC source | Modification method | IPDMSiCl/AGU molar ratio | Level of CNC loading relative to the oil phase | Was a 19:1 high internal phase emulsion formed? |
|---|---|---|---|---|---|
| 1A | None | N/A | N/A | 0.00% | Yes |
| 1B | tunicate mantles | No surface modification | 0.0 | 0.88% | No |
| 1C | tunicate mantles | isopropyldimethylchlorosilane (IPDMSiCl) | 2.0 | 0.88% | Yes |
| 1D | tunicate mantles | isopropyldimethylchlorosilane (IPDMSiCl) | 4.0 | 0.88% | Yes |
| 1E | tunicate mantles | isopropyldimethylchlorosilane (IPDMSiCl) | 6.0 | 0.88% | Yes |

TABLE 1B

| | CNC source | Modifying reagent for the CNCs | Level of CNC loading relative to the oil phase (wt. %) | Modulus (KPa) |
|---|---|---|---|---|
| 1 | — | — | — | 10.0 ± 0.0 |
| 2 | MxG-CNC | Acetic anhydride | 0.1 | 23.7 ± 2.3 |
| 3 | MxG-CNC | Acetic anhydride | 0.25 | 142.8 ± 25.3 |
| 4 | MxG-CNC | Acetic anhydride | 0.50 | 175.7 ± 9.0 |
| 5 | MxG-CNC | Acetic anhydride | 0.75 | 115.0 ± 33.4 |
| 6 | MxG-CNC | Acetic anhydride | 1.00 | 114.5 ± 27.0 |
| 7 | MxG-CNC | Acetic anhydride | 1.50 | 120.0 ± 42.9 |
| 8 | MxG-CNC | Butyric Anhydride | 0.25 | 17.0 ± 1.4 |
| 9 | MxG-CNC | Butyric Anhydride | 0.50 | 37.3 ± 3.4 |
| 10 | MxG-CNC | Butyric Anhydride | 1.00 | 64.0 ± 17.3 |
| 11 | MxG-CNC | Hexyl isocyanate | 1.00 | 9.3 ± 0.6 |
| 12 | MxG-CNC | — | 0.1 | 137.0 ± 15.4 |
| 13 | MxG-CNC | — | 0.25 | 138.0 ± 25.0 |

TABLE 1C

| | CNC source | Modifying reagent for the CNCs | Level of CNC loading versus oil phase (wt. %) | Modulus (KPa) |
|---|---|---|---|---|
| 1 | — | — | — | 227 ± 60 |
| 2 | MxG-CNC | Butyric Anhydride | 0.5 | 270 ± 3 |
| 3 | MxG-CNC | Butyric Anhydride | 1.0 | 350 ± 33 |
| 4 | MxG-CNC | Butyric Anhydride | 1.5 | 265 ± 59 |
| 5 | MxG-CNC | Butyric Anhydride | 2.0 | 300 ± 21 |
| 6 | MxG-CNC | Hexyl isocyanate | 1.0 | 268 ± 57 |

A series of three poly(HIPE)s were made to determine the wettability enhancement of adding CNC to the aqueous phase.

Step 1: CNC Preparation from TEMPO Mediated Oxidation of MCC

The microcrystalline cellulose (MCC) dry powder was used as received (Sigma-Aldrich 20 um). 2 g of MCC powder was stirred in 200 mL deionized water where 32 mg of 2,2,6,6-tetramethylpyperidine-1-oxyl (TEMPO) and 200 mg sodium bromide were already dissolved. Once no large MCC aggregates were observed in the suspension, TEMPO-mediated oxidation was initiated by adding dropwise the 7.45 g of the sodium hypochlorite solution (10-15%, Sigma-Aldrich). The pH of the oxidation system was kept at 10.0-10.5 by adding 0.5M sodium hydroxide aqueous solution. After oxidation at room temperature under mild magnetic stirring (~250 rpm) for 4 hrs, the oxidation reaction was terminated by adding 15 mL ethanol. The TEMPO-oxidized MCC was thoroughly washed three times with deionized water or until the pH is 7.0, then was dried by a lyophilizer for 3 days: the samples were first cooled down to −80° C., then the pressure was lowered to 50 micro bar, finally the temperature was increased to 25° C. and the samples were dried for 3 days.

Step 2: Preparation of CNC Aqueous Suspension

To prepare CNC aqueous suspensions, 80 mg/160 mg freeze-dried oxidized MCC was re-dispersed in deionized water (10 mL) in a 20 mL glass vial. A magnetic stir bar was added and stirring occurred for 10 min. Further dispersion was accomplished by inserting a 13 mm diameter probe from a Sonics & Materials ultrasonicator 15 mm in depth from the surface of the MCC dispersion. A 40% amplitude was selected. A cycle of 5 seconds sonication, 5 seconds no sonication occurred for a period of 30 min (the total ultra-sonication time was 15 min). After ultra-sonication, the CNC suspensions were totally transparent, which indicates a good dispersion of particles.

Step 3: Preparation of Emulsions with and without CNC in Aqueous Phase and Polymerization.

Figure 3:
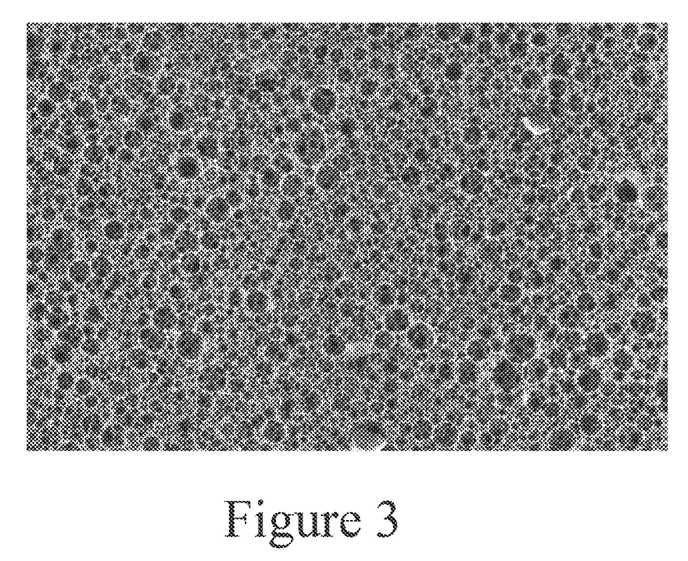
FIG. 3 is an SEM of an embodiment of the invention.

For 0.053 wt % final CNC concentration in the aqueous phase, 142 g of 2.1 wt % NaCl and approximately 0.3-0.5 wt % NaPS solution (40° C.) was first added dropwise into 8 g oil phase by a gear pump under 300 rpm agitation mixing in 3 min 6 sec to form an emulsion. The oil phase contains approximately 30-40% 2-EHMA, 30-40% 2-EHA, 10-20% EGDMA, less than 10% PGS, less than 10% DTDMAMS. The PGS and DTDMAMS surfactants were thoroughly dissolved in the monomer blend. Then the previous 80 mg CNC suspension (10 mL) was added by hand into this emulsion within 54 sec. The emulsion was mixed for another 1 minute before it was transferred into 50 mL centrifuge tubes (45 mL emulsion each tube) and cured at 85° C. in a convection oven. The final dispersed phase to oil phase weight ratio was 19:1. The initiator concentration in dispersed phase was 0.33 wt %. Thus the CNC concentration in dispersed phase was 0.053 wt %. This sample is named Sample 2B as found in Table 2 and FIG. 3.

Figure 4:
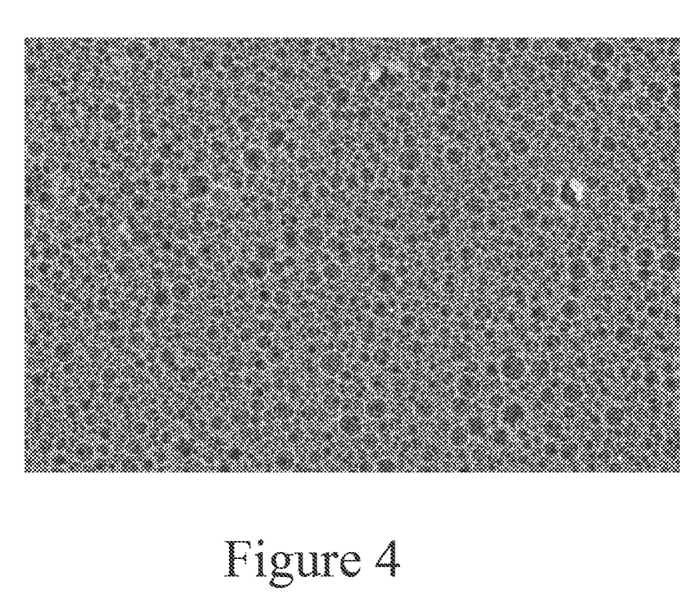
FIG. 4 is an SEM of an embodiment of the invention.

For 0.11 wt % final CNC concentration in the aqueous phase, 142 g of 2.1 wt % NaCl and approximately 0.3-0.5 wt % NaPS solution (40° C.) was first added dropwise into 8 g oil phase by a gear pump under 300 rpm agitation mixing in 3 min 6 sec to form an emulsion. The oil phase contains approximately 30-40% 2-EHMA, 30-40% 2-EHA, 10-20% EGDMA, less than 10% PGS, less than 10% DTDMAMS. The PGS and DTDMAMS surfactants were thoroughly dissolved in the monomer blend. Then the previous 160 mg CNC suspension (10 mL) was added by hand into this emulsion within 54 sec. The emulsion was mixed for another 1 minute before it was transferred into 50 mL centrifuge tubes (45 mL emulsion each tube) and cured at 85° C. in a convection oven. The final dispersed phase to oil phase weight ratio was 19:1. The initiator concentration in dispersed phase was 0.33 wt %. Thus the CNC concentration in dispersed phase was 0.106 wt % and the NaCl concentration in the dispersed phase was 2.0 wt %. This sample is named Sample 2C as found in Table 2 and FIG. 4.

Figure 2:
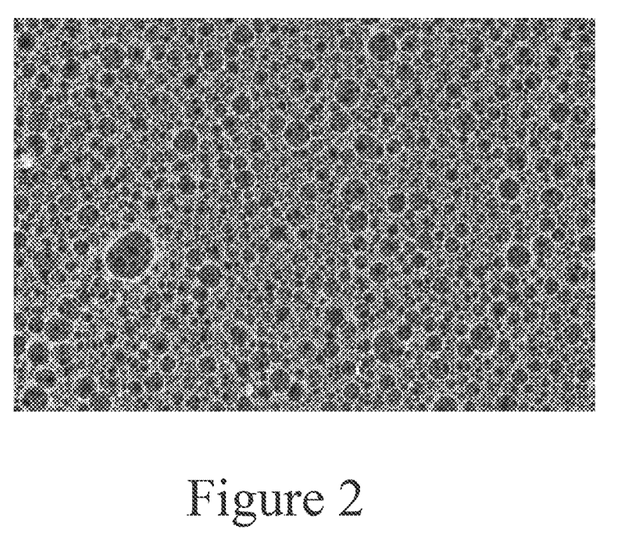
FIG. 2 is an SEM of a HIPE foam without cellulose nanoparticles.

A control (specimen made without CNC) polyHIPE foam was made by adding 142 g of 2 wt % NaCl by gear pump into 8 g oil phase under 300 rpm agitation mixing in 3 min 6 sec to form an emulsion. The oil phase contains approximately 30-40% 2-EHMA, 30-40% 2-EHA, 10-20% EGDMA, less than 10% PGS, less than 10% DTDMAMS. The PGS and DTDMAMS surfactants were thoroughly dissolved in the monomer blend. Less than 100 g initiator solution was added into this emulsion within 54 sec and the emulsion was mixed for another 1 minute before it was transferred into a capped 50 mL centrifuge tubes (45 mL emulsion each tube) and cured at 85° C. in a convection oven. The final dispersed phase to oil phase was 19:1. This sample is named Sample 2A as found in Table 2 and FIG. 2.

| Sample name | CNC precursor | CNC Concentration | Washburn Coefficient, C $(mg^2/s)$ |
|---|---|---|---|
| 2A | None | 0 | $7.66 * 10^3$ |
| 2B | MCC | 0.053% CNC | $2.35 * 10^5$ |
| 2C | MCC | 0.106% CNC | $3.10 * 10^4$ |

Step 4: Preparation of the PolyHIPE Foams

After 24 hrs the samples were taken out of the oven and cooled down to room temperature. The cured wet cylindrical polyHIPE foams were then sliced into 15 mm thick discs (25 mm in diameter) for further tests. The small disc shape foams were put on a PTFE plate and dried in 85° C. convection oven for 24 hrs. NaCl was left inside the polyHIPE foams after drying. The dried foams were weighed and then preserved into small plastic sample bags. A small shape disc from each polyHIPE was analyzed for SEM and the results indicate that the D32 (Sauter mean diameter) cell size changed from 18.4 micron for the control (2A) to 17.9 micron for the 0.053 wt% CNC (2B) and 13.3 micron for 0.11 wt% CNC (2C). Images of the foams from Scanning Electron Microscopy (SEM) are found in FIGS. 2, 3, and 4.

Step 5: Water Uptake Test for Characterizing PolyHIPE Foams Absorbency Ability

Figure 5:
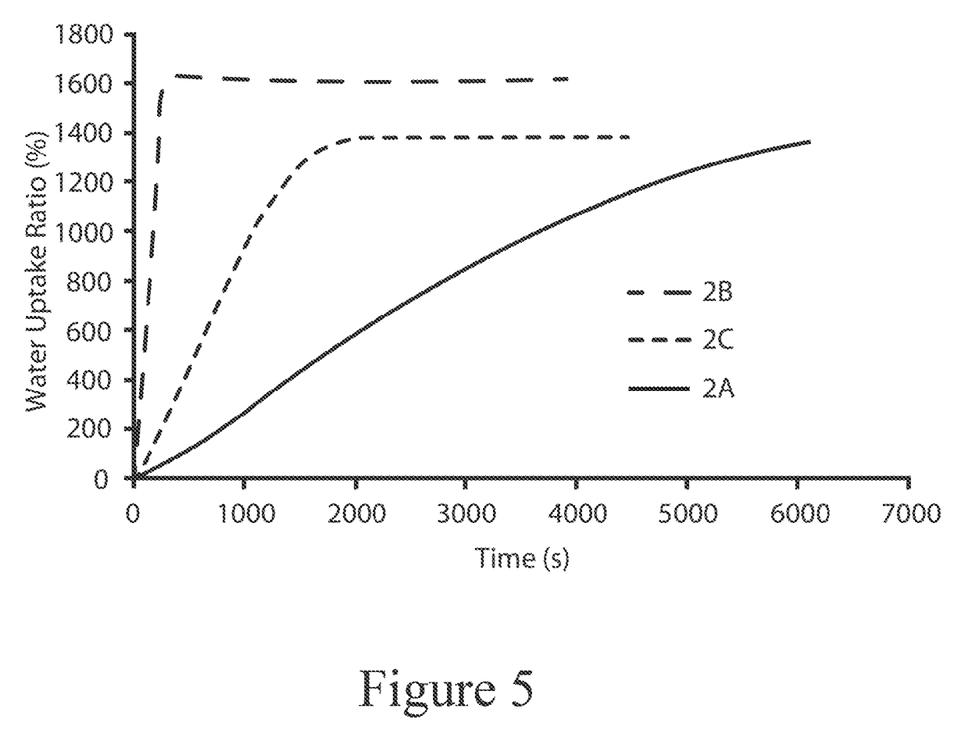
FIG. 5 is a graph showing water uptake for various samples.

A piece of dried polyHIPE foam from step 4 was inserted to one end of a polypropylene cylinder (the same 50 mL centrifuge tube from step 3 were machined so that both ends of the cylinder were open) so that the bottom of the tube is flush with the bottom of the foam. The tube was attached vertically to a homemade stand which sat on a microbalance (resolution 0.1 mg, maximum 110 g). The bottom of the tube was then brought into contact with DI water allowing the liquid to contact the foam surface and thus wick the water upwards into the foam. The mass of the water being absorbed by the foam was recorded by a computer which was connected to the balance through a serial port. A plot of water absorbed versus time for each sample is shown in FIG. 5. The % water absorbed is calculated as the mass of the absorbed water/the mass of the dry foam (exclusive of NaCl). The result was fitted to the Washburn equation, wherein m is the mass of water absorbed, t is the time, and C represents the mass squared divided by the time, to obtain the Washburn coefficient, C:

$$m^2 = C * t$$

A High Internal Phase Emulsion (HIPE) foam is disclosed. The HIPE is formed by polymerizing a High Internal Phase Emulsion comprising: a) an oil phase comprising i) monomer; ii) cross-linking agent; iii) emulsifier; iv) cellulose nanoparticles; and b) an aqueous phase. The High Internal Phase Emulsion foam may exhibit a compression modulus of between 20 KPa and 200 KPa. The cellulose nanoparticles may be present in an amount between about 0.001% and 5% by weight of the oil phase. The cellulose nanoparticles may be Microfibrillated cellulose (MFC), Microcrystalline cellulose (MCC), Nanocrystalline cellulose (NCC), Nano cellulose or Nanocellulose or Bacterial nanocellulose, Nanofibrillated cellulose (NFC), Cellulose nanofiber(s), Cellulose microfibril or cellulosic microfibril(s), Cellulose nanorod or cellulosic nanorod(s), Cellulose nanocrystal(s) (CNC), or combinations thereof. The aqueous phase may comprise an initiator.

The cellulose nanoparticles may be modified by a surface modification prior to insertion into the oil or aqueous phase to make the cellulose nanoparticles more hydrophobic. The surface modification agent may be selected from isopropyldimethylchlorosilane (IPDMSiCl), cetyltrimethylammonium bromide (CTAB), butyric anhydride (BA), Octadecylamine (CONH-C18), (2-dodecen-1-yl)succinic anhydride (DDy SA), Octadecyl isocyanate (U-C18), Hexyl isocyanate (U-C6), 2-Ethylhexyl Isocyanate, Acetic anhydride (A), and combinations thereof. The surface modification may be combined with 2,2,6,6-tetramethylpyperidine-1-oxyl (TEMPO) with sodium hypochlorite (NaClO) (TEMPO/NaClO) or (2-dodecen-1-yl)succinic anhydride (DDy SA), Sulfuric acid ($SO_3^-$). The initiator may be at least one of ammonium persulfate, sodium persulfate, potassium persulfate, or 2,2'-azobis(N,N'-dimethyleneisobutyramidine)dihydrochloride. The monomer may be alkyl acrylate or alkyl methacrylate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising an absorbent core, the absorbent core comprising a high internal phase emulsion foam formed by polymerizing a high internal phase emulsion comprising:
   a) an oil phase comprising:
      i) a monomer comprising a substantially water-insoluble monofunctional alkyl acrylate or alkyl methacrylate, constituting from about 20% to about 97% by weight of the oil phase;
      ii) a cross-linking agent;
      iii) an emulsifier;
      iv) cellulose nanoparticles; and
   b) an aqueous phase comprising a water-soluble electrolyte,
   wherein the foam is an open-cell foam wherein at least about 80% of cells in the foam that are at least 1 μm in size are in fluid communication with at least one adjoining cell; and
   wherein the high internal phase emulsion has a water-to-oil ratio of 13:1 to 65:1.

2. The absorbent article of claim 1, wherein the high internal phase emulsion foam is a polyHIPE.

3. The absorbent article of claim 1, wherein the high internal phase emulsion foam has a compression modulus of between about 20 KPa and about 400 KPa.

4. The absorbent article of claim 1, wherein the cellulose nanoparticles are present in an amount between about 0.001% and about 5% by weight of the oil phase.

5. The absorbent article of claim 1, wherein the cellulose nanoparticles comprise at least one of microfibrillated cellulose (MFC), microcrystalline cellulose (MCC), nanocrystalline cellulose (NCC), nanocellulose, nanofibrillated cellulose (NFC), a cellulose nanofiber, a cellulose microfibril, a cellulose nanorod, a cellulose nanocrystal (CNC), or combinations thereof.

6. The absorbent article of claim 1, wherein the aqueous phase comprises an initiator.

7. The absorbent article of claim 1, wherein the cellulose nanoparticles are modified by a surface modification prior to insertion into the oil phase to make the cellulose nanoparticles more hydrophobic.

8. The absorbent article of claim 1, wherein the cellulose nanoparticles have an aspect ratio between about 10 to about 130.

9. The absorbent article of claim 7, wherein the surface modification is performed with a species selected from the group consisting of 2,2,6,6-tetramethylpyperidine-1-oxyl (TEMPO) with sodium hypochlorite (NaClO) (TEMPO/NaClO) oxidized, isopropyldimethylchlorosilane (IPDM-SiCl), butyric anhydride (BA), cetyltrimethylammonium bromide (CTAB), Octadecylamine (CONH-C18), (2-dodecen-1-yl)succinic anhydride (DDy SA), Sulfuric acid ($SO_3^-$) and then (2-dodecen-1-yl)succinic anhydride (DDy SA), Octadecyl isocyanate (U-C18), Hexyl isocyanate (U-C6), 2-Ethylhexyl Isocyanate, Acetic anhydride (A), and combinations thereof.

10. The absorbent article of claim 6, wherein the initiator is at least one of ammonium persulfate, sodium persulfate, potassium persulfate, or 2,2'-azobis(N,N'-dimethyleneisobutyramidine)dihydrochloride.

11. An absorbent article comprising an absorbent core, the absorbent core comprising a high internal phase emulsion foam formed by polymerizing a high internal phase emulsion comprising:
   a) an oil phase comprising:
      i) a monomer comprising a substantially water-insoluble monofunctional alkyl acrylate or alkyl methacrylate, constituting from about 20% to about 97% by weight of the oil phase;
      ii) a cross-linking agent;
      iii) an emulsifier;
      iv) cellulose nanoparticles; and
   b) an aqueous phase comprising a water-soluble electrolyte,
   wherein the foam is an open-cell foam.

12. The absorbent article of claim 11, wherein the high internal phase emulsion foam is a polyHIPE.

13. The absorbent article of claim 11, wherein the high internal phase emulsion foam has a compression modulus of between about 20 KPa and about 400 KPa.

14. The absorbent article of claim 11, wherein the cellulose nanoparticles are present in an amount between about 0.001% and about 5% by weight of the oil phase.

15. The absorbent article of claim 11, wherein the cellulose nanoparticles comprise at least one of microfibrillated cellulose (MFC), microcrystalline cellulose (MCC), nanocrystalline cellulose (NCC), nanocellulose, nanofibrillated cellulose (NFC), a cellulose nanofiber, a cellulose microfibril, a cellulose nanorod, a cellulose nanocrystal (CNC), or combinations thereof.

16. The absorbent article of claim 11, wherein the aqueous phase comprises an initiator.

17. The absorbent article of claim 11, wherein the cellulose nanoparticles are modified by a surface modification prior to insertion into the oil phase to make the cellulose nanoparticles more hydrophobic.

18. The absorbent article of claim 11, wherein the cellulose nanoparticles have an aspect ratio between about 10 to about 130.

19. The absorbent article of claim 17, wherein the surface modification is performed with a species selected from the group consisting of 2,2,6,6-tetramethylpyperidine-1-oxyl (TEMPO) with sodium hypochlorite (NaClO) (TEMPO/NaClO) oxidized, isopropyldimethylchlorosilane (IPDM-SiCl), butyric anhydride (BA), cetyltrimethylammonium bromide (CTAB), Octadecylamine (CONH-C18), (2-dodecen-1-yl)succinic anhydride (DDy SA), Sulfuric acid ($SO_3^-$) and then (2-dodecen-1-yl)succinic anhydride (DDy SA), Octadecyl isocyanate (U-C18), Hexyl isocyanate (U-C6), 2-Ethylhexyl Isocyanate, Acetic anhydride (A), and combinations thereof.

20. The absorbent article of claim 16, wherein the initiator is at least one of ammonium persulfate, sodium persulfate, potassium persulfate, or 2,2'-azobis(N,N'-dimethyleneisobutyramidine)dihydrochloride.

* * * * *